(12) United States Patent
Govea et al.

(10) Patent No.: US 10,485,969 B2
(45) Date of Patent: Nov. 26, 2019

(54) ELECTRICAL STIMULATION CUFF DEVICES AND SYSTEMS

(71) Applicant: Boston Scientific Neuromodulation Corporation, Valencia, CA (US)

(72) Inventors: Michael X. Govea, Glendale, CA (US); William George Orinski, Reno, NV (US); William Conrad Stoffregen, Lake Elmo, MN (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 97 days.

(21) Appl. No.: 15/436,544

(22) Filed: Feb. 17, 2017

(65) Prior Publication Data

US 2017/0239462 A1    Aug. 24, 2017

Related U.S. Application Data

(60) Provisional application No. 62/297,616, filed on Feb. 19, 2016.

(51) Int. Cl.
*A61N 1/05* (2006.01)
*A61N 1/36* (2006.01)
*A61N 1/375* (2006.01)

(52) U.S. Cl.
CPC ......... *A61N 1/0556* (2013.01); *A61N 1/0558* (2013.01); *A61N 1/36003* (2013.01); *A61N 1/3605* (2013.01); *A61N 1/3752* (2013.01)

(58) Field of Classification Search
CPC ... A61N 1/0556; A61N 1/0558; A61N 1/3605
See application file for complete search history.

(56) References Cited

U.S. PATENT DOCUMENTS 3,769,984 A    11/1973   Muench
3,941,136 A    3/1976    Bucalo
(Continued)

FOREIGN PATENT DOCUMENTS

WO    98/37926    9/1998
WO    98/43700    10/1998
(Continued)

OTHER PUBLICATIONS

U.S. Appl. No. 12/177,823, Entitled: Lead With Transition and Methods of Manufacture and Use, Inventor: Pianca et al., filed Jul. 22, 2008, 22 pages.
(Continued)

*Primary Examiner* — Eric D. Bertram
(74) *Attorney, Agent, or Firm* — Lowe Graham Jones PLLC; Bruce E. Black

(57) ABSTRACT

An electrical stimulation lead includes a stimulation cuff having an exterior surface and an interior surface that defines a nerve channel having a nerve channel axis. A plurality of electrodes are disposed on the interior surface of the cuff. A longitudinal opening extends through the cuff and further extends along an entire length of the cuff, wherein the opening is operable to receive a target nerve from a region outside of the cuff to within the nerve channel. A mount is disposed on the exterior surface of the cuff and radially offset from the nerve channel axis. A lead body is radially offset from the nerve channel axis and a plurality of conductors extend through the lead body, mount and cuff, with the plurality of conductors electrically coupled to the electrodes. The electrical stimulation lead may include a plurality of slots to permit tissue ingrowth.

20 Claims, 8 Drawing Sheets

(56) References Cited

U.S. PATENT DOCUMENTS

| | | |
|---|---|---|
| 4,033,357 A | 7/1977 | Helland et al. |
| 4,135,518 A | 1/1979 | Dutcher |
| 4,257,428 A | 3/1981 | Barton et al. |
| 4,301,815 A | 11/1981 | Doring |
| 4,409,994 A | 10/1983 | Doring |
| 4,475,560 A | 10/1984 | Tarjan et al. |
| 4,506,679 A | 3/1985 | Mann |
| 4,542,753 A | 9/1985 | Brenman et al. |
| 4,585,005 A | 4/1986 | Lue et al. |
| 4,628,944 A | 12/1986 | MacGregor et al. |
| 4,702,254 A | 10/1987 | Zabara |
| 4,716,888 A | 1/1988 | Wesner |
| 4,722,353 A | 2/1988 | Sluetz |
| 4,796,643 A | 1/1989 | Nakazawa et al. |
| 4,867,164 A | 9/1989 | Zabara |
| 4,920,979 A | 5/1990 | Bullara |
| 4,934,368 A | 6/1990 | Lynch |
| 4,957,118 A | 9/1990 | Erlebacher |
| 5,025,807 A | 6/1991 | Zabara |
| 5,095,905 A | 3/1992 | Klepinski |
| 5,139,539 A | 8/1992 | Haynes, Jr. |
| 5,143,067 A | 9/1992 | Rise et al. |
| 5,193,539 A | 3/1993 | Schulman et al. |
| 5,193,540 A | 3/1993 | Schulman et al. |
| 5,239,540 A | 8/1993 | Rovira et al. |
| 5,251,634 A | 10/1993 | Weinberg |
| 5,257,634 A | 11/1993 | Kroll |
| 5,282,468 A | 2/1994 | Klepinski |
| 5,312,439 A | 5/1994 | Loeb |
| 5,314,457 A | 5/1994 | Jeutter et al. |
| 5,324,322 A | 6/1994 | Grill et al. |
| 5,324,327 A | 6/1994 | Cohen |
| 5,376,108 A | 12/1994 | Collins et al. |
| 5,405,367 A | 4/1995 | Schulman et al. |
| 5,433,735 A | 7/1995 | Zanakis et al. |
| 5,439,938 A | 8/1995 | Synder et al. |
| 5,454,840 A | 10/1995 | Krakovsky et al. |
| 5,480,420 A | 1/1996 | Hoegnelid et al. |
| 5,487,756 A | 1/1996 | Kallesoe et al. |
| 5,531,781 A | 7/1996 | Alferness et al. |
| 5,571,118 A | 11/1996 | Boutos |
| 5,741,319 A | 4/1998 | Woloszko et al. |
| 5,755,762 A | 5/1998 | Bush |
| 5,775,331 A | 7/1998 | Raymond et al. |
| 5,876,399 A | 3/1999 | Chia et al. |
| 5,919,220 A | 7/1999 | Stieglitz et al. |
| 5,922,015 A | 7/1999 | Schaldach et al. |
| 5,938,584 A | 8/1999 | Ardito et al. |
| 6,051,017 A | 4/2000 | Loeb et al. |
| 6,058,332 A | 5/2000 | Dahl |
| 6,061,596 A | 5/2000 | Richmond et al. |
| 6,151,526 A | 11/2000 | Tziviskos |
| 6,175,710 B1 | 1/2001 | Kamaji et al. |
| 6,175,764 B1 | 1/2001 | Loeb et al. |
| 6,181,965 B1 | 1/2001 | Loeb et al. |
| 6,181,969 B1 | 1/2001 | Fielding et al. |
| 6,181,973 B1 | 1/2001 | Ceron et al. |
| 6,185,452 B1 | 2/2001 | Schulman et al. |
| 6,185,455 B1 | 2/2001 | Loeb et al. |
| 6,188,932 B1 | 2/2001 | Lindegren |
| 6,201,994 B1 | 3/2001 | Warman et al. |
| 6,214,032 B1 | 4/2001 | Loeb et al. |
| 6,224,450 B1 | 5/2001 | Norton |
| 6,271,094 B1 | 8/2001 | Boyd et al. |
| 6,278,897 B1 | 8/2001 | Rutten et al. |
| 6,292,703 B1 | 9/2001 | Meier et al. |
| 6,295,944 B1 | 10/2001 | Lovett |
| 6,308,105 B1 | 10/2001 | Duysens et al. |
| 6,315,721 B2 | 11/2001 | Schulman et al. |
| 6,364,278 B1 | 4/2002 | Lin et al. |
| 6,391,985 B1 | 5/2002 | Goode et al. |
| 6,456,866 B1 | 9/2002 | Tyler et al. |
| 6,463,335 B1 | 10/2002 | Munch et al. |
| 6,516,227 B1 | 2/2003 | Meadows et al. |
| 6,582,441 B1 | 6/2003 | He et al. |
| 6,584,363 B2 | 6/2003 | Heil, Jr. et al. |
| 6,600,956 B2* | 7/2003 | Maschino ............ A61N 1/0556 607/118 |
| 6,609,029 B1 | 8/2003 | Mann et al. |
| 6,609,032 B1 | 8/2003 | Woods et al. |
| 6,643,546 B2 | 11/2003 | Mathis et al. |
| 6,650,943 B1 | 11/2003 | Whitehurst et al. |
| 6,735,474 B1 | 5/2004 | Loeb et al. |
| 6,741,892 B1 | 5/2004 | Meadows et al. |
| 6,788,975 B1 | 9/2004 | Whitehurst et al. |
| 7,003,352 B1 | 2/2006 | Whitehurst |
| 7,006,875 B1 | 2/2006 | Kuzma et al. |
| 7,203,548 B2 | 4/2007 | Whitehurst et al. |
| 7,244,150 B1 | 7/2007 | Brase et al. |
| 7,248,930 B1 | 7/2007 | Woloszko et al. |
| 7,292,890 B2 | 11/2007 | Whitehurst et al. |
| 7,437,193 B2 | 10/2008 | Parramon et al. |
| 7,450,997 B1 | 11/2008 | Pianca et al. |
| 7,460,913 B2 | 12/2008 | Kuzma et al. |
| 7,584,004 B2 | 9/2009 | Caparso et al. |
| 7,596,414 B2 | 9/2009 | Whitehurst et al. |
| 7,610,103 B2 | 10/2009 | Whitehurst et al. |
| 7,672,734 B2 | 3/2010 | Anderson et al. |
| 7,706,892 B2 | 4/2010 | Colvin et al. |
| 7,761,165 B1 | 7/2010 | He et al. |
| 7,783,359 B2 | 8/2010 | Meadows |
| 7,783,362 B2 | 8/2010 | Whitehurst et al. |
| 7,792,590 B1 | 9/2010 | Pianca et al. |
| 7,809,446 B2 | 10/2010 | Meadows |
| 7,840,279 B2 | 11/2010 | He |
| 7,949,395 B2 | 5/2011 | Kuzma |
| 7,953,498 B1 | 5/2011 | Carbunaru et al. |
| 7,974,706 B2 | 7/2011 | Moffitt et al. |
| 8,019,443 B2 | 9/2011 | Schleicher et al. |
| 8,155,757 B1 | 4/2012 | Neisz et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,483,237 B2 | 7/2013 | Zimmermann et al. |
| 8,594,805 B2 | 11/2013 | Hincapie Ordonez et al. |
| 8,612,025 B2 | 12/2013 | Neisz et al. |
| 8,688,235 B1 | 4/2014 | Pianca et al. |
| 8,718,790 B2 | 5/2014 | Pianca |
| 8,768,488 B2 | 7/2014 | Barker |
| 8,818,524 B2 | 8/2014 | Hincapie Ordonez et al. |
| 8,831,742 B2 | 9/2014 | Pianca et al. |
| 8,849,422 B2 | 9/2014 | Pianca |
| 8,934,992 B2 | 1/2015 | Johnson et al. |
| 2003/0040785 A1 | 2/2003 | Maschino et al. |
| 2003/0045919 A1 | 3/2003 | Swoyer et al. |
| 2003/0074039 A1 | 4/2003 | Puskas |
| 2003/0078623 A1 | 4/2003 | Weinberg et al. |
| 2003/0114905 A1 | 6/2003 | Kuzma |
| 2003/0199938 A1 | 10/2003 | Smits et al. |
| 2003/0236558 A1 | 12/2003 | Whitehurst et al. |
| 2004/0010303 A1 | 1/2004 | Bolea et al. |
| 2004/0034401 A1 | 2/2004 | Dahlberg et al. |
| 2004/0059392 A1 | 3/2004 | Parramon et al. |
| 2004/0111139 A1 | 6/2004 | McCreery |
| 2004/0230280 A1 | 11/2004 | Cates et al. |
| 2005/0010265 A1 | 1/2005 | Baru Fassio et al. |
| 2005/0065589 A1 | 3/2005 | Schneider et al. |
| 2005/0177220 A1 | 8/2005 | Iaizzo et al. |
| 2005/0182472 A1 | 8/2005 | Wahlstrom et al. |
| 2006/0161204 A1 | 7/2006 | Colvin et al. |
| 2006/0184204 A1 | 8/2006 | He |
| 2006/0212075 A1 | 9/2006 | Marnfeldt |
| 2006/0241737 A1 | 10/2006 | Tockman et al. |
| 2006/0282145 A1 | 12/2006 | Caparso et al. |
| 2007/0150036 A1 | 6/2007 | Anderson |
| 2007/0219595 A1 | 9/2007 | He |
| 2008/0046055 A1 | 2/2008 | Durand et al. |
| 2008/0071320 A1 | 3/2008 | Brase |
| 2008/0103545 A1* | 5/2008 | Bolea ................. A61N 1/0556 607/42 |
| 2009/0187222 A1 | 7/2009 | Barker |

(56) References Cited

U.S. PATENT DOCUMENTS

| | | |
|---|---|---|
| 2009/0276021 A1 | 11/2009 | Meadows et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2010/0049276 A1 | 2/2010 | Blum et al. |
| 2010/0076535 A1 | 3/2010 | Pianca et al. |
| 2010/0241207 A1* | 9/2010 | Bluger ............ A61B 5/0422 607/118 |
| 2010/0268298 A1 | 10/2010 | Moffitt et al. |
| 2010/0298916 A1 | 11/2010 | Rabischong et al. |
| 2011/0004267 A1 | 1/2011 | Meadows et al. |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0316615 A1 | 12/2012 | Digiore et al. |
| 2013/0023974 A1 | 1/2013 | Amrani |
| 2013/0105071 A1 | 5/2013 | Digiore et al. |
| 2013/0172973 A1 | 7/2013 | Tockman et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317518 A1 | 11/2013 | Govea |
| 2013/0317587 A1 | 11/2013 | Barker |
| 2013/0325091 A1 | 12/2013 | Pianca et al. |
| 2014/0039587 A1 | 2/2014 | Romero |
| 2014/0074213 A1 | 3/2014 | Neisz et al. |
| 2014/0094887 A1* | 4/2014 | True ............ A61N 1/0556 607/118 |
| 2014/0094888 A1* | 4/2014 | True ............ A61N 1/0556 607/118 |
| 2014/0188202 A1* | 7/2014 | Zarembo ............ A61N 1/0556 607/118 |
| 2014/0277284 A1 | 9/2014 | Chen et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0174396 A1* | 6/2015 | Fisher ............ A61N 1/0556 600/377 |
| 2015/0202433 A1 | 7/2015 | Franke et al. |
| 2015/0202446 A1 | 7/2015 | Franke et al. |
| 2015/0366467 A1 | 12/2015 | De Kock et al. |
| 2017/0224982 A1 | 8/2017 | Nageri et al. |

FOREIGN PATENT DOCUMENTS

| | | |
|---|---|---|
| WO | 98/43701 | 10/1998 |
| WO | 2008019483 A1 | 2/2008 |
| WO | 2008048471 A2 | 4/2008 |
| WO | 2013188871 A1 | 12/2013 |

OTHER PUBLICATIONS

U.S. Appl. No. 13/750,725, Entitled: Systems and Methods for Identifying the Circumferential Positioning of Electrodes of Leads for Electrical Stimulation Systems, Inventor: Pianca et al., filed Jan. 25, 2013, 36 pages.

U.S. Appl. No. 62/292,096, Entitled: Slotted Sleeve Neurostimulation Device, Inventor: Ranjan Krishna Mukhari Nageri et al., filed Feb. 6, 2016, 32 pages.

U.S. Appl. No. 62/297,616, Entitled: Electrical Stimulation Cuff Devices and Systems, Inventor: Ranjan Krishna Mukhari Nageri et al., filed Feb. 19, 2016, 34 pages.

U.S. Appl. No. 15/424,481, Entitled: Slotted Sleeve Neurostimulation Device, Inventor: Ranjan Krishna Mukhari Nageri et al., filed Feb. 17, 2017, 29 pages.

International Search Report and Written Opinion for International Patent Application No. PCT/US2017/018467, dated Apr. 12, 2017.

Rattay, F., "Analysis of Models for External Stimulation of Axons," IEEE Transactions on Biomedical Engineering, BME-33(10): 974-977, 1986.

U.S. Appl. No. 15/601,838, filed May 22, 2017.

U.S. Appl. No. 15/608,573, filed May 30, 2017.

U.S. Appl. No. 62/429,650, filed Dec. 2, 2016.

U.S. Appl. No. 15/656,734, filed Jul. 21, 2017.

Rozman et al., "Selective Stimulation of Autonomic Nerves and Recording of Electroneurograms in a Canine Model," Artificial Organs, 21(8): 592-596, 2008.

Polasek et al., "Stimulation Stability and Selectivity of Chronically Implanted Multicontact Nerve Cuff Electrodes in the Human Upper Extremity," IEEE Transactions on Neural Systems and Rehabilitation Engineering, vol. 17, No. 5, 428-437, Oct. 2009.

Plachta et al., "Blood pressure control with selective vagal nerve stimulation and minimal side effects," J. Neural Eng. 11 (2014) 036011 (15pp), 2014.

\* cited by examiner

ELECTRICAL STIMULATION CUFF DEVICES AND SYSTEMS

CROSS-REFERENCE TO RELATED APPLICATIONS

This application claims the benefit under 35 U.S.C. § 119(e) of U.S. Provisional Patent Application Ser. No. 62/297,616, filed Feb. 19, 2016, which is incorporated herein by reference.

FIELD

The present invention is directed to the area of implantable electrical stimulation systems and methods of making and using the systems. The present invention is also directed to implantable electrical stimulation cuff devices, as well as methods of making and using the same.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead that includes a stimulation cuff having an exterior surface and an interior surface that defines a nerve channel having a nerve channel axis. A plurality of electrodes are disposed on the interior surface of the cuff. A longitudinal opening extends through the cuff and further extends along an entire length of the cuff, wherein the opening is operable to receive a target nerve from a region outside of the cuff to within the nerve channel. Further, a mount is disposed on the exterior surface of the cuff and is radially offset from the nerve channel axis. A lead body, with a lead body axis, is radially offset from the nerve channel axis and a plurality of conductors extend through the lead body, mount and cuff, with the plurality of conductors electrically coupled to the electrodes.

In at least some embodiments, the cuff defines at least one slot that extends less than the entire length of the cuff. The slot can be located between at least two of the electrodes. The slot may permit tissue ingrowth at least from the exterior surface of the cuff into the nerve channel. The cuff can also include end portions for receiving sutures.

In at least some embodiments, the electrical stimulation lead includes cuff stiffeners embedded in the cuff proximate the longitudinal opening. At least one of the cuff stiffeners can extend less than the entire length of the cuff. Or, at least one of the cuff stiffeners can extend the entire length of the cuff. The cuff stiffeners can be cylindrical.

Another embodiment is an electrical stimulating system that includes the electrical stimulation lead described above. The system further includes a control module coupleable to the electrical stimulation lead includes a housing, and an electronic subassembly disposed in the housing. The system also includes a connector for receiving the electrical stimulation lead, the connector having a proximal end, a distal end, and a longitudinal length. The connector includes a connector housing and a plurality of connector contacts disposed in the connector housing. The connector housing defines a port at the distal end of the connector, the port receiving the proximal end of the lead body of the electrical stimulation lead. The plurality of connector contacts couple to at least one of a plurality of terminals disposed on a proximal end of the lead body of the electrical stimulation lead. In at least some embodiments, the system also includes a lead extension coupleable to both the electrical stimulation lead and the control module.

In at least some embodiments, an electrical stimulation lead includes a stimulation cuff having a cuff body with an interior surface and an exterior surface, the interior surface defines a nerve channel having a nerve channel axis. A plurality of electrodes are disposed on the interior surface of the cuff body. A longitudinal opening extends through the cuff body and further extends along an entire length of the cuff body. The opening is operable to receive a target nerve from a region outside of the cuff to within the nerve channel. A plurality of slots, to permit tissue ingrowth, each extends through the cuff body and each has a length that is less than the entire length of the cuff body. The electrical stimulation lead also includes a lead body having a lead body axis and a plurality of conductors extending through the lead body, mount and cuff, such that the plurality of conductors are electrically coupled to the electrodes.

In at least some embodiments, a mount is disposed on the exterior surface of the cuff body and coupled to the lead body such that the lead body axis is radially offset from the nerve channel axis of the cuff body.

In at least some embodiments, at least one of the plurality of slots is located between at least two of the electrodes. The cuff body includes end portions configured to receive sutures. Further, cuff stiffeners, which may be cylindrical, may be embedded in the cuff body proximate the longitudinal opening.

Yet another embodiment is an electrical stimulating system that includes the electrical stimulation lead described above. The system includes a control module coupleable to the electrical stimulation lead, and the control module includes a housing, and an electronic subassembly disposed in the housing. The system further includes a connector for receiving the electrical stimulation lead, the connector having a proximal end, a distal end, and a longitudinal length. The connector includes a connector housing and a plurality of connector contacts disposed in the connector housing. The connector defines a port at the distal end of the connector for receiving the proximal end of the lead body of the electrical stimulation lead. The plurality of connector contacts couple to at least one of a plurality of terminals disposed on a proximal end of the lead body of the electrical stimulation lead. In at least some embodiments, the system also includes a lead extension coupleable to both the electrical stimulation lead and the control module.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation cuff devices, as well as methods of making and using the same.

Suitable implantable electrical stimulation systems include, but are not limited to, a least one lead with one or more electrodes disposed along a distal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,203,548; 7,244,150; 7,450,997; 7,596,414; 7,610,103; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entireties.

Figure 1:
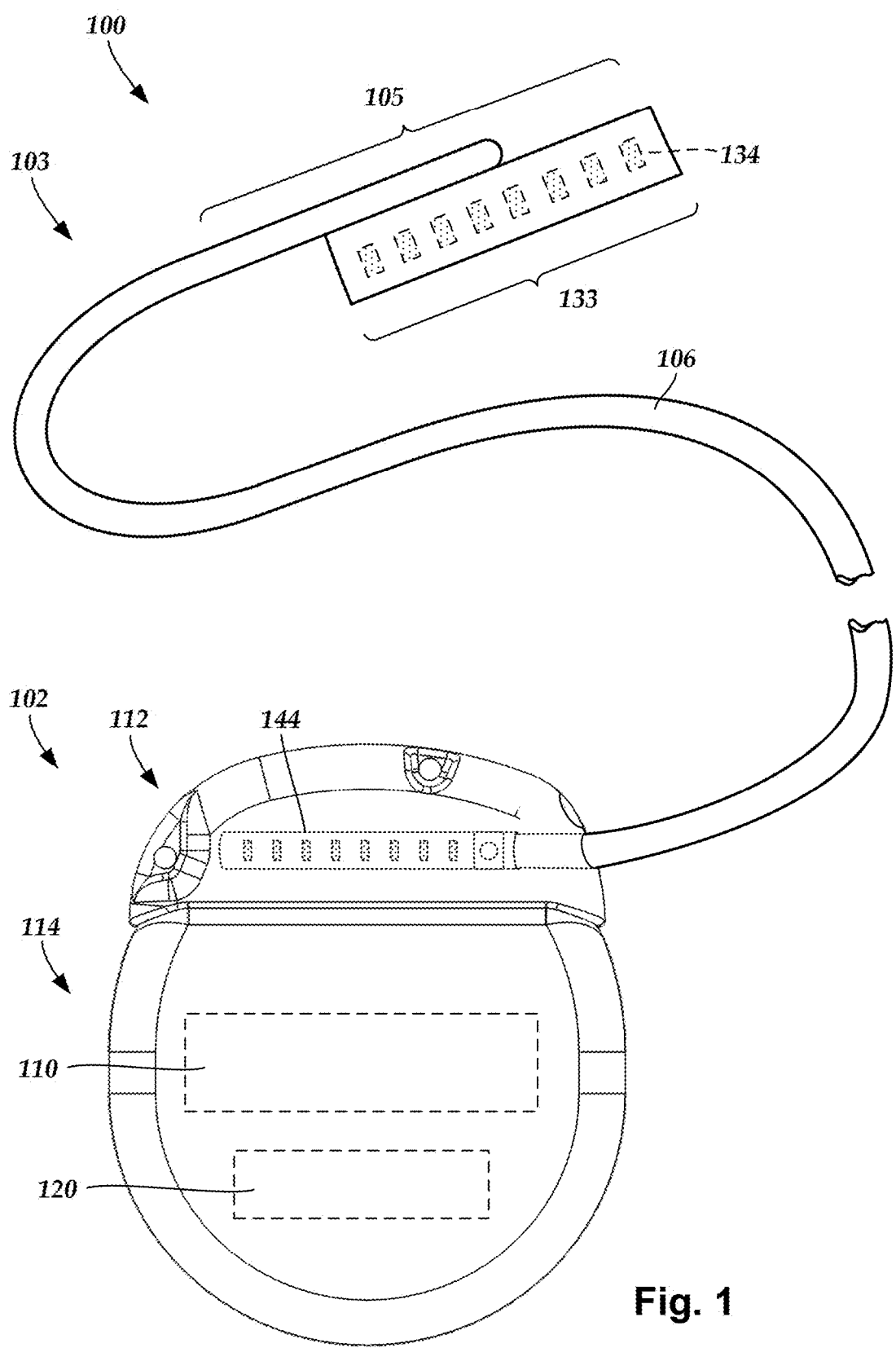
FIG. 1 is a schematic view of one embodiment of an electrical stimulation system that includes a lead electrically coupled to a control module according to an embodiment of the present invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a distal end portion 105, shown schematically, but will be described in detail below (e.g., a distal end portion 300 in FIGS. 3A-3D and a distal end portion 400 in FIGS. 4A-4C. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. Stimulation circuitry 110 and an optional power source 120 are disposed in the electronics housing 114. A control module connector 144 is disposed in the connector housing 112. The control module connector 144 is configured and arranged to make an electrical connection between the lead 103 and the stimulation circuitry 110 of the control module 102.

The electrical stimulation system or components of the electrical stimulation system, including the lead body 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the lead body 106 are typically disposed in, or separated by, a non-conductive, biocompatible material such as, for example, silicone, polyurethane, polyetheretherketone ("PEEK"), epoxy, and the like or combinations thereof. The lead body 106 may be formed in the desired shape by any process including, for example, molding (including injection molding), casting, and the like. The non-conductive material typically extends from the distal end of the lead body 106 to the proximal end of the lead body 106.

Figure 2A:
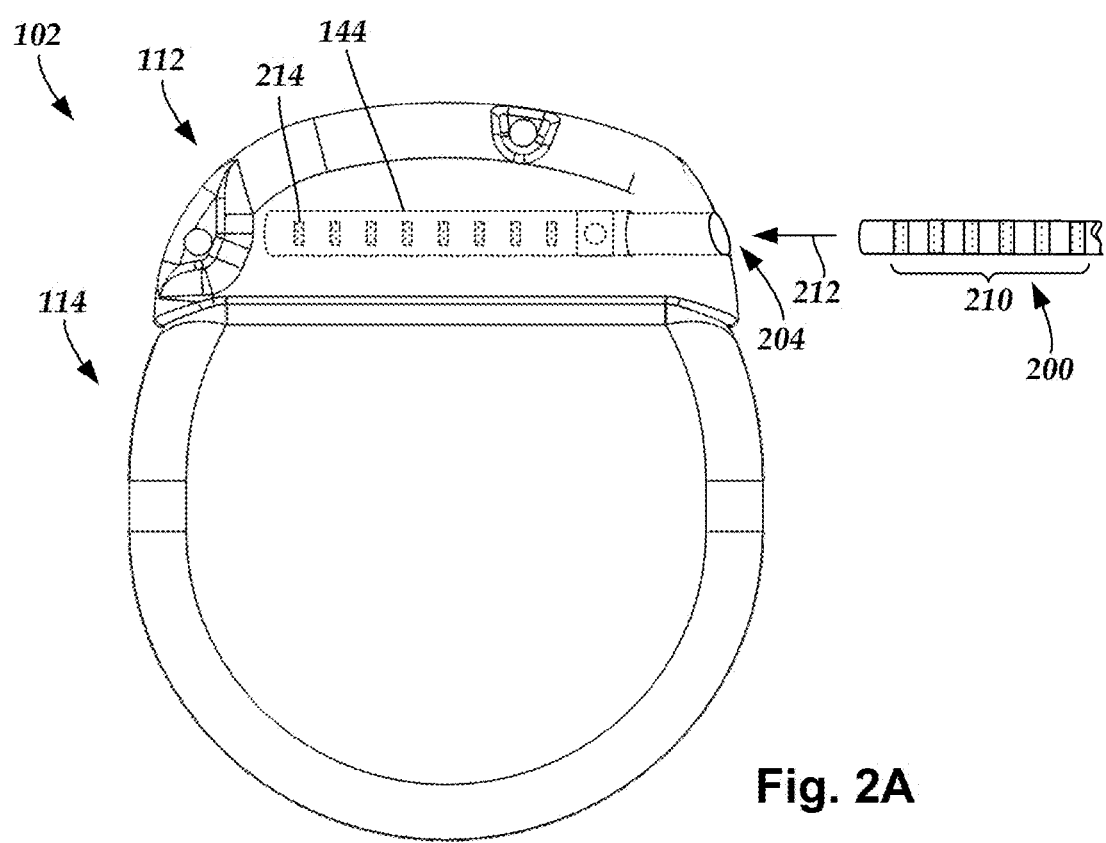
FIG. 2A is a schematic view of one embodiment of the control module of FIG. 1 configured and arranged to electrically couple to an elongated device according to an embodiment of the present invention.
Figure 2B:
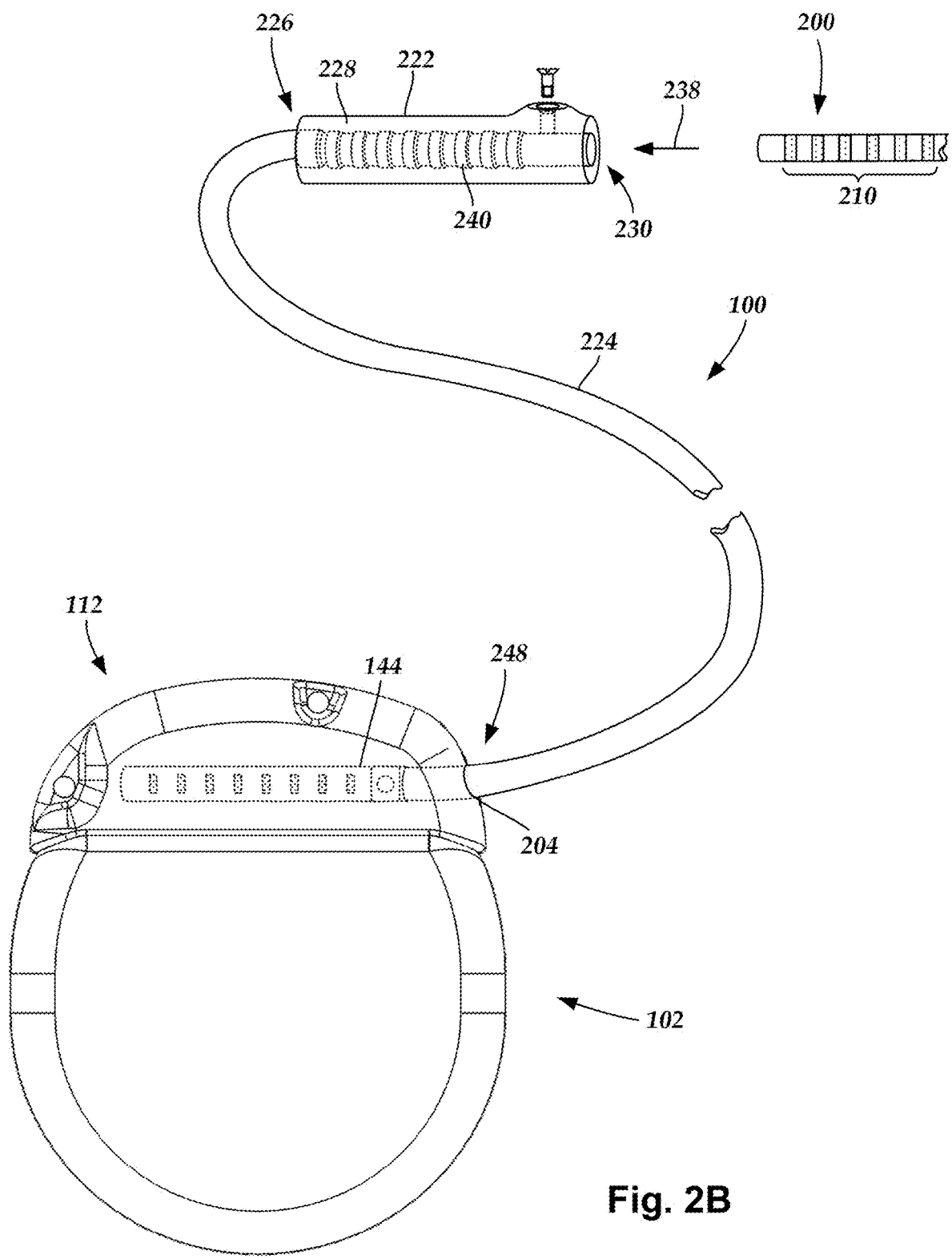
FIG. 2B is a schematic view of one embodiment of a lead extension configured and arranged to electrically couple the elongated device of FIG. 2A to the control module of FIG. 1 according to an embodiment of the present invention.

Terminals (e.g., 210 in FIGS. 2A-2B) are typically disposed along the proximal end of the lead body 106 of the electrical stimulation system 100 (as well as any splitters, lead extensions, adaptors, or the like) for electrical connection to corresponding connector contacts (e.g., 214 and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the lead body 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the lead extension 224 of FIG. 2B, an adaptor, or the like or combinations thereof), or a combination thereof.

The control module connector 144 defines at least one port into which a proximal end of the elongated device 200 can be inserted, as shown by directional arrow 212. In FIG. 2A (and in other figures), the connector housing 112 is shown having one port 204. The connector housing 112 can define any suitable number of ports including, for example, one, two, three, four, five, six, seven, eight, or more ports.

The control module connector 144 also includes a plurality of connector contacts, such as connector contact 214, disposed within each port 204. When the elongated device 200 is inserted into the port 204, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103.

Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

In at least some instances, a large control module, such as the control module 102 illustrated in FIGS. 1-2B, is not desirable. A smaller, more compact control module may be suitable for situations such as, for example, short-term implantation (for example, 1 or 2 weeks, 1, 2, 3, 4, 6, 8, 12, or 18 months), short-term trial (for example, 1 or 2 weeks, 1, 2, 3, 4, 6, 8, 12, or 18 months), clinical studies (for example, for a period of 1 or 2 weeks, 1, 2, 3, 4, 6, 8, 12, or 18 months), or the like. Such a control module may also be useful when a less invasive surgical implantation is desired, recommended, or required. In some instances, a patient or clinician may be willing to charge the control module more frequently if the control module is smaller or the surgery is less invasive. In addition, there may be more options in the body of the patient for implantation of a smaller control module than are available for the larger control module (which is often implanted in the thoracic body cavity or the buttocks due to the size of the device.) A smaller control module may also be less expensive and particularly useful for trials to determine whether electrical stimulation is beneficial. In at least some embodiments, the electrical stimulation system with the smaller control module can be upgraded to an electrical stimulation system such as that illustrated in FIGS. 1-2B if the trial shows sufficient benefit to the patient. In at least some embodiments, the smaller control module may allow for the device to be MRI (magnetic resonance imaging) conditionally safe because of its implant location and size.

In some embodiments, the control module can be made smaller by permanently affixing the lead (or a lead extension) to the control module. For example, the lead can be hardwired to the stimulation circuitry so that the control module does not need a connector and header.

Figure 3A:
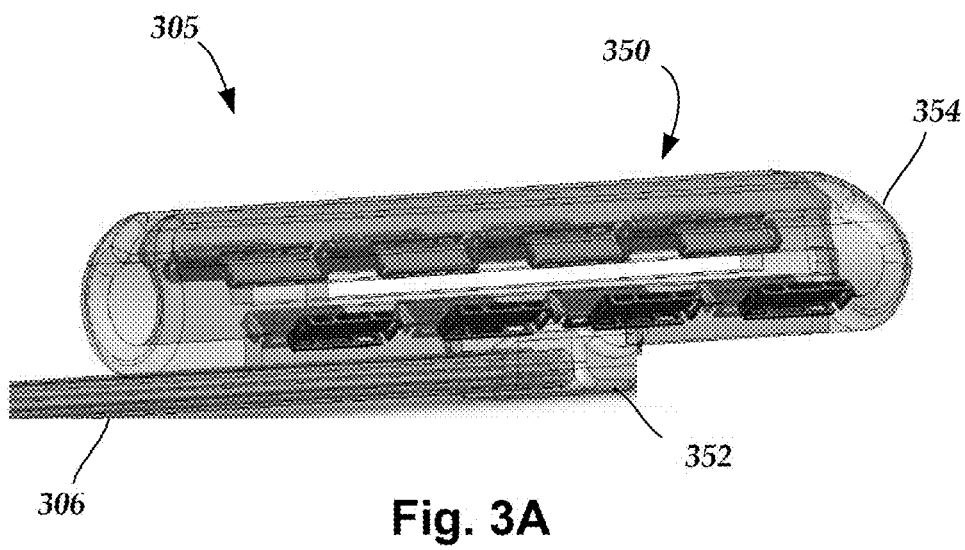
FIG. 3A is a schematic perspective view of a distal end portion of a lead that includes a stimulation cuff according to an embodiment of the present invention.

FIG. 3A illustrates, schematically, a distal end portion 305 of the lead 103 (FIG. 1) that includes a cuff 350 with a cuff body 354, a mount 352 and a lead body 306 according to an embodiment of the present invention. The lead body 306 can be, for example, structurally the same or similar to the lead body 106 (FIG. 1), operates in a same or similar manner, and may be manufactured in accordance with one or more of the methods disclosed in U.S. Patent Application No. 2007/0150036, which is hereby incorporated by reference in its entirety, or in accordance with other methods or references cited herein.

In at least some embodiments, the cuff 350 permits stimulation of a target nerve (not shown), for example a peripheral nerve located in soft tissue, and may be small in diameter. By way of example, the cuff 350 can operate to provide vagus or sympathetic nerve stimulation. When using many conventional leads to stimulate the target nerve, it may be difficult to initiate and maintain contact between the conventional lead and the target nerve. In at least some embodiments, the cuff 350 may advantageously permit an easier implantation around the target nerve than conventional cuff leads that wrap helically around the target nerve. In at least some embodiments, the cuff 350 may also permit selective stimulation of different regions of the target nerve. The number of electrodes 334 as well as the arrangement of the electrodes 334 can vary depending on the type of nerve being stimulated, a region of the nerve being stimulated, or any combination thereof.

The electrodes 334 can be formed using any conductive, biocompatible material. Examples of suitable materials include metals, alloys, conductive polymers, conductive carbon, and the like, as well as combinations thereof. In at least some embodiments, one or more of the electrodes 334 are formed from one or more of: platinum, platinum iridium, palladium, palladium rhodium, or titanium. The electrodes 334 may take the form of segmented electrodes, have a variety of shapes such as, but not limited to, a concave, convex or otherwise curved shape, a box shape, a dish or parabolic shape, or any combination thereof. In at least some embodiments, the electrodes 334 may take the form of segmented electrodes having a shape complementary to a body or carrier onto which they are disposed.

Any suitable number of electrodes 334 can be disposed on the cuff body 354 including, for example, four, five, six, seven, eight, nine, ten, eleven, twelve, fourteen, sixteen, twenty-four, thirty-two, or more electrodes 334. The electrodes 334 may be arranged into columns or rows. In at least some embodiments, one column includes four electrodes 334. The arrangement of the electrode(s) 334 may vary. For example, the electrodes 334 may be arranged in two or more parallel columns where such columns can be aligned or staggered from one another, or in any other desired column or row arrangement. The electrodes may also be arranged, for example, in a row, or "in line," along the longitudinal axis of a small diameter lead body. Optionally, the electrodes may be placed linearly, circularly, or elliptically. The arrangement of electrodes may be symmetrical or asymmetrical. As will be recognized, other arrangements of electrodes are also possible.

The electrodes 334 can be disposed on the cuff body 354 in any suitable arrangement. In at least some embodiments, an inward facing surface of the electrode 334 is flush with an inner surface of the cuff body 354. In yet other embodiments, the inward facing surface of the electrode 334 is recessed relative to the inner surface of the cuff body 354.

The lead body 306, cuff body 354 and the mount 352 can be made from a non-conductive, biocompatible material such as, for example, silicone, polyurethane, polyetheretherketone ("PEEK"), epoxy, and the like or combinations thereof. The lead body 306 and the cuff body 354 may be formed in the desired shape by any process including, for example, molding (including injection molding), casting, and the like.

In at least some embodiments, the cuff body 354 is made from silicone with electrodes 334 disposed in the silicone cuff body 354. The cuff 350 may be manufactured by molding the electrodes 334 into the cuff body 354 while allowing for electrode alignment. In an initial step, the electrodes 334 are molded into a thin, silicone carrier that allows for electrode alignment. Next, conductors (not shown) from the lead body 306 are connected (e.g., welded) to a backside of the electrodes 334. Lastly, the carrier is wrapped around a pin or rod and then overmolded into the cuff body 354.

In at least some embodiments, the conductors (not shown) from within the lead body 306 are received in the mount 352, which in turn is attached to the cuff body 354 such that each conductor passes through the mount 352 for a direct electrical connection with one of the electrodes 334 (e.g., one conductor is electrically connected with one electrode and so on). The mount 352 may be attached using a variety of means such as, but not limited to, molding or adhering the mount 352 to the cuff body 354. In other embodiments, the conductors from within the lead body 306 are electrically coupled to the electrodes 334 using jumper, intermediate or transition wires from the lead body 306 to the electrodes 334.

Figure 3B:
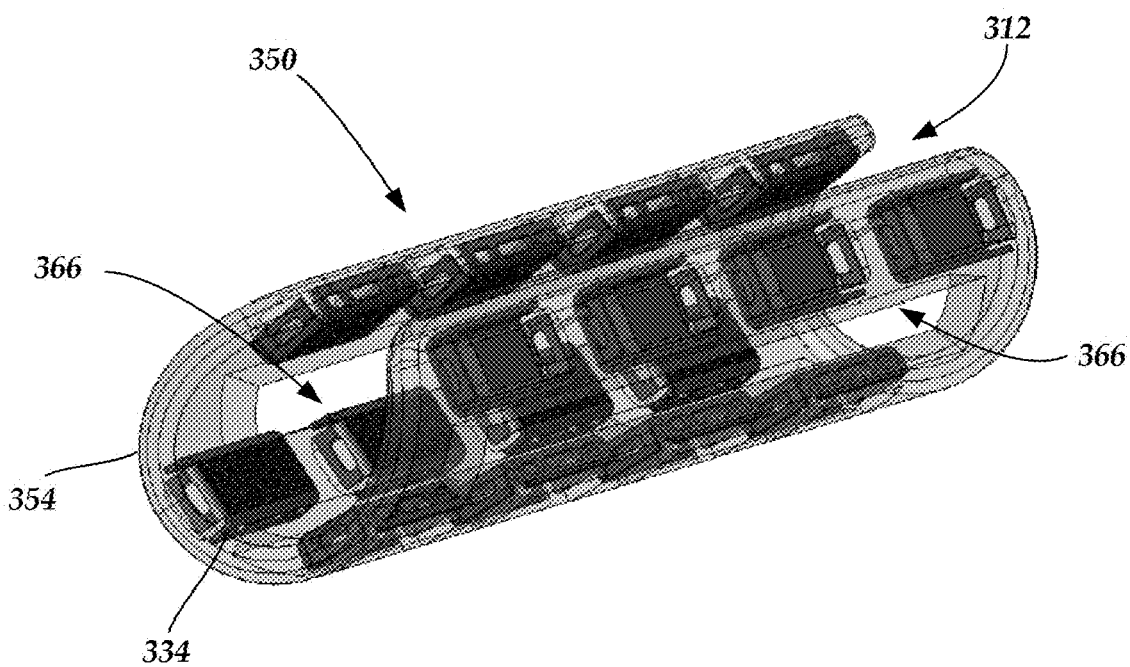
FIG. 3B is a schematic, perspective close-up view of the cuff of FIG. 3A according to an embodiment of the present invention.
Figure 3C:
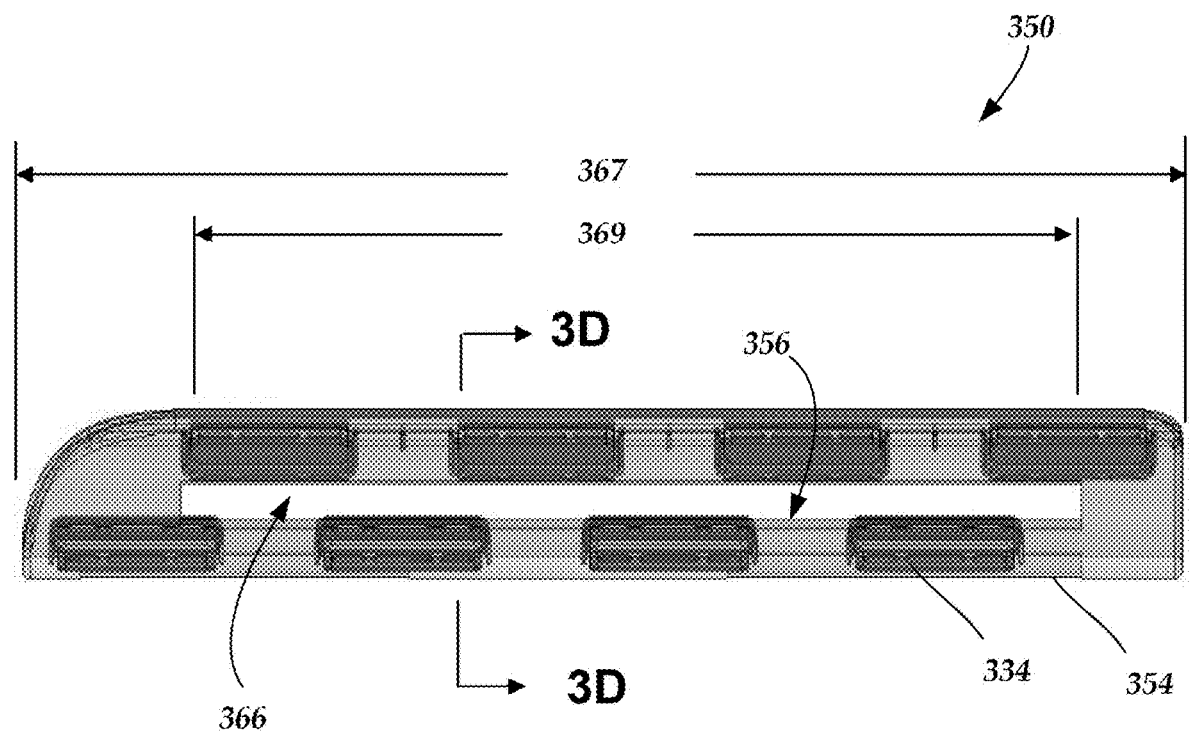
FIG. 3C is a side elevational view of the cuff of FIG. 3B according to an embodiment of the present invention.
Figure 3D:
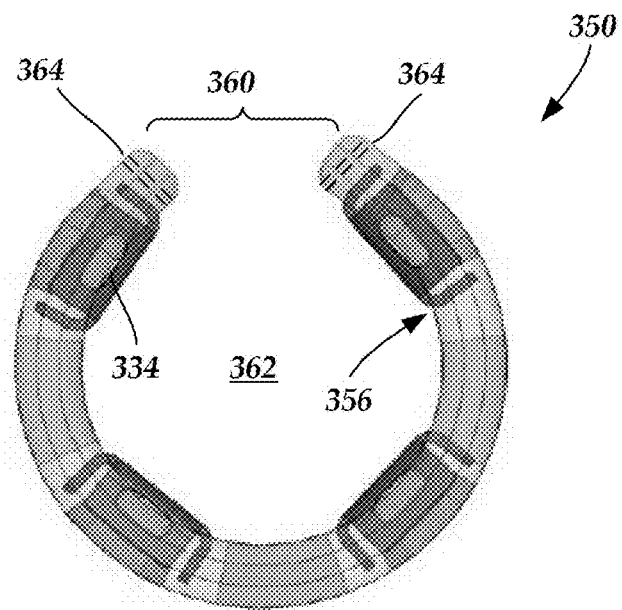
FIG. 3D is a cross-sectional view of the cuff of FIG. 3B taken along line 3D-3D according to an embodiment of the present invention.

FIGS. 3B-3D show the cuff 350 having the plurality of electrodes 334 disposed on an inner surface 356 of the cuff body 354. In the illustrated embodiment of FIG. 3B, the cuff body 354 takes the form of a C-shaped cuff having the inner surface 356, an outer surface 358, and a longitudinal opening 360 that extends through both the outer surface 358 and inner surface 356 of the cuff body 354. As noted above, formation of the cuff 350 into the "C-shape" can include the steps of wrapping and overmolding to form the cuff body 354 in which the inner surface 356 defines a nerve channel 362 (best seen in FIG. 3D).

The opening 360 is manipulated or initially sized to allow the target nerve (not shown) to be slipped, inserted, fed or otherwise received into nerve channel 362 of the cuff 350 such that the cuff 350 wraps around the target nerve. In at least some embodiments, the opening 360 allows the cuff 350 to be easily moved over and around the target nerve or relative to the target nerve whether rotationally or transitionally. By way of example, the cuff 350 may be rotated, translated or otherwise repositioned, if needed, along a target nerve axis 470 (FIG. 4B) that is parallel to or approximately parallel to a longitudinal axis of the nerve channel 362. Repositioning of the cuff 350 may permit intimate or selected stimulation between a particular region of the target nerve and one or more of the electrodes 334.

In at least some embodiments, once the cuff 350 has been placed in a desired position relative to the target nerve, the edges of the cuff body 354 defining the opening 360 can be sutured to capture the target nerve without undesirably compressing the target nerve. In at least some embodiments, suture holes 364 (FIG. 3D) are optionally incorporated into the edges of the cuff 350 to allow for closing or partially closing the cuff 350 around the target nerve. Moreover, at least in some embodiments, the suture holes 364 can be used as points of manipulation or tool attachment during implantation (e.g., using forceps or an equivalent tool).

Referring to FIGS. 3B and 3C, in at least some embodiments, the cuff 350 includes one or more longitudinal slots 366 located between individual, adjacently-located electrodes 334 or rows of electrodes. In at least some embodiments, the slots 366 are sized and arranged to decrease a structural stiffness of the cuff 350. In at least some embodiments, the slots 366 provide for tissue ingrowth, which may eventually help anchor the cuff 350 relative to the target nerve after implantation. The slots 366 may generally have a rectangular shape, but other shapes such as elliptical are possible. The slots 366 extends some portion of a full length 367 of the cuff body 354. By way of example, a slot length 369 may be up to ten (10) percent, up to twenty (20) percent, up to thirty (30) percent, up to forty (40) percent, or up to fifty (50) percent of the full length 367 of the cuff body 354. Alternatively, the slot length 369 may be more than fifty (50) percent, more than sixty (60) percent, more than seventy (70) percent, more than eighty (80) percent, or more than ninety (90) percent of the full length 367 of the cuff body 354.

Figure 4A:
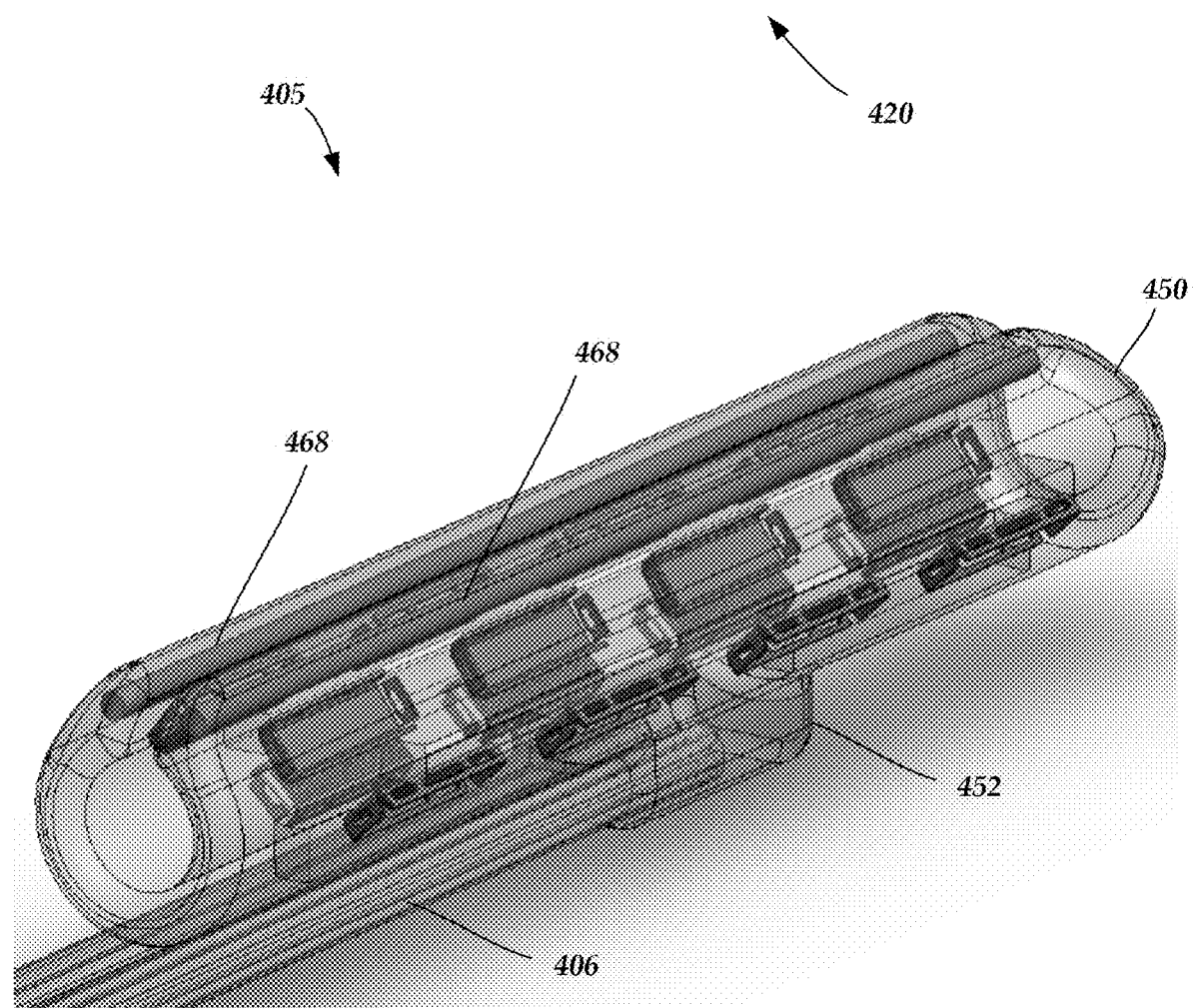
FIG. 4A is a schematic perspective view of a distal end portion of a lead that includes a stimulation cuff having cuff stiffeners according to an embodiment of the present invention.

FIG. 4A illustrates, schematically, another distal end portion 405 for the lead 103 (FIG. 1) that includes a cuff 450, a mount 452, a lead body 406, and cuff stiffeners 468 according to an embodiment of the present invention. Similar to the mount shown in FIG. 3A, the mount 452 may be attached to the cuff 450 such as, but not limited to, molding or adhering.

Figure 4B:
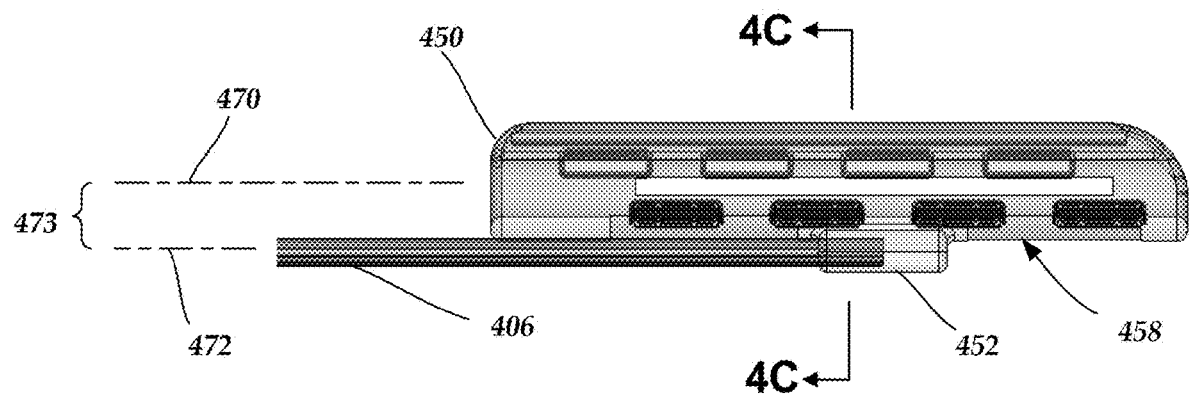
FIG. 4B is a side elevational view of the cuff of FIG. 4A according to an embodiment of the present invention.

Referring to FIG. 4B, the mount 452 is attached to an exterior surface 458 of the cuff 450, which in turn allows for easier cuff implantation because a target nerve axis 470 is offset 473 from a lead body axis 472. In at least some of the embodiments, the offset 473 preferably operates to prevent the lead body 406 and the target nerve (not shown) from coming into physical contact downstream of the cuff 450 after implantation.

Figure 4C:
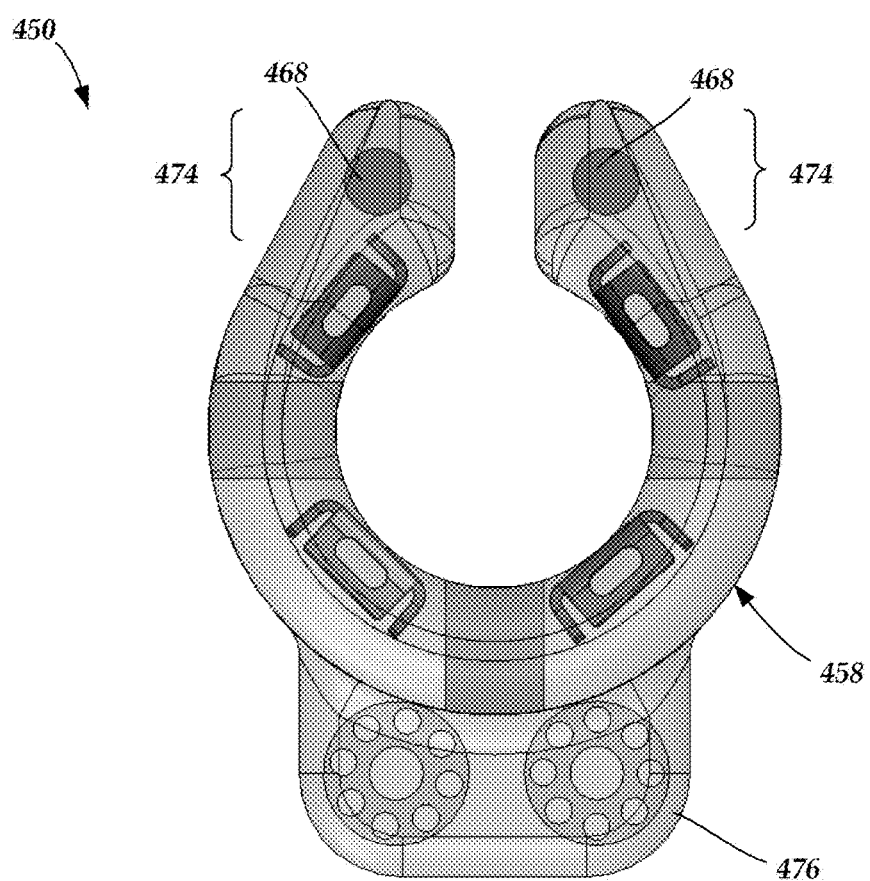
FIG. 4C is a cross-sectional view of the cuff of FIG. 4B taken along line 4C-4C according to an embodiment of the present invention.

FIG. 4C shows a cross-section of the cuff 450 with the cuff stiffeners 468 located in end portions 474 thereof. The cuff stiffeners 468 can be molded into the end portions 474 of the cuff 450 or inserted after molding of the cuff 450. In at least some embodiments, the cuff stiffeners 468 may be sized and configured to make the end portions 474 of the cuff 450 easier to manipulate around the target nerve during implantation without significantly affecting an overall stiffness of the cuff 450. The cuff stiffeners 468 may extend approximately the length of the cuff 450 or may be shorter such that a plurality of cuff stiffeners 468 may be linearly placed in the end portions 474. An overall length of one cuff stiffener may be up to ten (10) percent, up to twenty (20) percent, up to thirty (30) percent, up to forty (40) percent, or up to fifty (50) percent of the full length 367 (FIG. 3C) of the cuff body 354. Alternatively, an overall length of one cuff stiffener may be more than fifty (50) percent, more than sixty (60) percent, more than seventy (70) percent, more than eighty (80) percent, or more than ninety (90) percent of the full length 367 (FIG. 3C) of the cuff body 354.

The cuff stiffeners 468 may be cylindrical or any other shape. In addition, the cuff stiffeners 468 may be made from a single material or more than one material to modify a bending stiffness of the cuff 450. By way of example, the cuff stiffeners 468 may be made from a rigid plastic or a metal material. Lastly, a mount 476 may take the form of a dual lead body mount attached to the outer surface 458 of the cuff 450, again offsetting the lead bodies from the target nerve.

Figure 5:
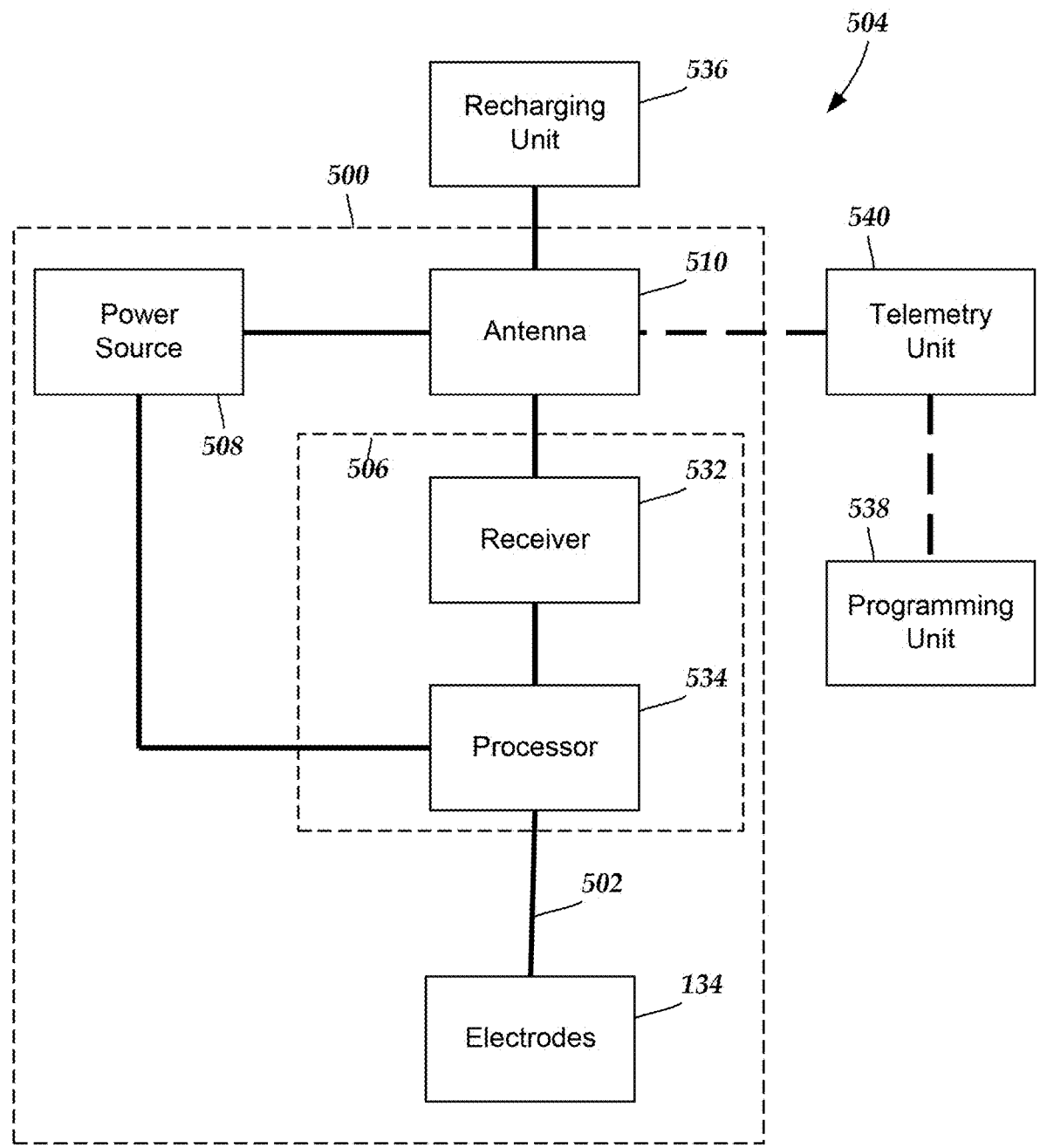
FIG. 5 is a schematic overview of one embodiment of components of an electrical stimulation arrangement according to an embodiment of the present invention.

FIG. 5 is a schematic overview of one embodiment of components of an electrical stimulation arrangement 504 that includes an electrical stimulation system 500 with a lead 502, stimulation circuitry 506, a power source 508, and an antenna 510. The electrical stimulation system can be, for example, any of the electrical stimulation systems described above. It will be understood that the electrical stimulation arrangement can include more, fewer, or different components and can have a variety of different configurations including those configurations disclosed in the stimulator references cited herein.

If the power source 508 is a rechargeable battery or chargeable capacitor, the power source may be recharged/charged using the antenna 510, if desired. Power can be provided for recharging/charging by inductively coupling the power source 508 through the antenna 510 to a recharging unit 536 external to the user. Examples of such arrangements can be found in the references identified above.

In at least some embodiments, electrical current is emitted by the electrodes (such as electrodes 134 in FIG. 1) on the lead 502 to stimulate nerve fibers, muscle fibers, or other body tissues near the electrical stimulation system. The stimulation circuitry 506 can include, among other components, a processor 534 and a receiver 532. The processor 534 is generally included to control the timing and electrical characteristics of the electrical stimulation system. For example, the processor 534 can, if desired, control one or more of the timing, frequency, strength, duration, and waveform of the pulses. In addition, the processor 534 can select which electrodes can be used to provide stimulation, if desired. In some embodiments, the processor 534 selects which electrode(s) are cathodes and which electrode(s) are anodes. In some embodiments, the processor 534 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 538 that, for example, allows modification of pulse characteristics. In the illustrated embodiment, the processor 534 is coupled to a receiver 532 which, in turn, is coupled to the antenna 510. This allows the processor 534 to receive instructions from an external source to, for example, direct the pulse characteristics and the selection of electrodes, if desired.

In at least some embodiments, the antenna 510 is capable of receiving signals (e.g., RF signals) from an external telemetry unit 540 that is programmed by the programming unit 538. The programming unit 538 can be external to, or part of, the telemetry unit 540. The telemetry unit 540 can be a device that is worn on the skin of the user or can be carried by the user and can have a form similar to a pager, cellular phone, or remote control, if desired. As another alternative, the telemetry unit 540 may not be worn or carried by the user but may only be available at a home station or at a clinician's office. The programming unit 538 can be any unit that can provide information to the telemetry unit 540 for transmission to the electrical stimulation system 500. The programming unit 538 can be part of the telemetry unit 540 or can provide signals or information to the telemetry unit 540 via a wireless or wired connection. One example of a suitable programming unit is a computer operated by the user or clinician to send signals to the telemetry unit 540.

The signals sent to the processor 534 via the antenna 510 and the receiver 532 can be used to modify or otherwise direct the operation of the electrical stimulation system 500. For example, the signals may be used to modify the pulses of the electrical stimulation system such as modifying one or more of pulse duration, pulse frequency, pulse waveform, and pulse strength. The signals may also direct the electrical stimulation system 500 to cease operation, to start operation, to start charging the battery, or to stop charging the battery.

Optionally, the electrical stimulation system 500 may include a transmitter (not shown) coupled to the processor 534 and the antenna 510 for transmitting signals back to the telemetry unit 540 or another unit capable of receiving the signals. For example, the electrical stimulation system 500 may transmit signals indicating whether the electrical stimulation system 500 is operating properly or not or indicating when the battery needs to be charged or the level of charge remaining in the battery. The processor 534 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead comprising:
   a stimulation cuff having a cuff length, an exterior surface, and an interior surface that defines a nerve channel having a nerve channel axis, wherein the stimulation cuff defines at least one slot extending through the stimulation cuff with the stimulation cuff defining a perimeter around an entirety of each of the at least one slot at both the exterior surface and the interior surface of the stimulation cuff, wherein each of the at least one slot has a slot length that extends more than 50%, but less than 100%, of the cuff length;
   a plurality of electrodes disposed on the interior surface of the stimulation cuff, wherein the plurality of electrodes is arranged into a plurality of rows with each row extending parallel to the nerve channel axis, wherein each of the rows comprises at least two of the electrodes, wherein each of the at least one slot is disposed between two of the rows of the electrodes with at least two of the electrodes of each of the two rows disposed adjacent opposing sides of the respective slot;
   a longitudinal opening extending through the stimulation cuff and further extending along the entire cuff length of the stimulation cuff, the longitudinal opening operable to receive a target nerve from a region outside of the stimulation cuff to within the nerve channel;
   a mount disposed on the exterior surface of the stimulation cuff and radially offset from the nerve channel axis;
   a lead body having a lead body axis radially offset from the nerve channel axis; and
   a plurality of conductors extending through the lead body, mount and cuff, with the plurality of conductors electrically coupled to the electrodes.

2. The electrical stimulation lead of claim 1, wherein the stimulation cuff includes end portions configured to receive sutures.

3. The electrical stimulation lead of claim 1, further comprising cuff stiffeners embedded in the stimulation cuff proximate the longitudinal opening, wherein the cuff stiffeners are made of rigid plastic.

4. The electrical stimulation lead of claim 3, wherein at least one of the cuff stiffeners extends less than the entire cuff length of the stimulation cuff.

5. The electrical stimulation lead of claim 3, wherein at least one of the cuff stiffeners extends the entire cuff length of the stimulation cuff.

6. The electrical stimulation lead of claim 3, wherein the cuff stiffeners are cylindrical.

7. An electrical stimulating system comprising:
   the electrical stimulation lead of claim 1;
   a control module coupleable to the electrical stimulation lead, the control module comprising
      a housing, and
      an electronic subassembly disposed in the housing; and
   a connector for receiving the electrical stimulation lead, the connector having a proximal end, a distal end, and a longitudinal length, the connector comprising
      a connector housing defining a port at the distal end of the connector, the port configured and arranged for receiving a proximal end of the lead body of the electrical stimulation lead, and
      a plurality of connector contacts disposed in the connector housing, the plurality of connector contacts configured and arranged to couple to at least one of a plurality of terminals disposed on a proximal end of the lead body of the electrical stimulation lead.

8. The electrical stimulation system of claim 7, further comprising a lead extension coupleable to both the electrical stimulation lead and the control module.

9. The electrical stimulation lead of claim 1, wherein each of the at least one slot has a rectangular shape.

10. The electrical stimulation lead of claim 1, wherein the slot length of each of the at least one slot is more than 70% of the cuff length.

11. The electrical stimulation lead of claim 1, wherein the electrodes of at least one of the rows of electrodes are longitudinally staggered relative to the electrodes of another one of the rows.

12. An electrical stimulation lead comprising:
   a stimulation cuff having a cuff body with a cuff length, an interior surface, and an exterior surface, the interior surface defining a nerve channel having a nerve channel axis;
   a plurality of electrodes disposed on the interior surface of the cuff body, wherein the plurality of electrodes is arranged into a plurality of rows with each row extending parallel to the nerve channel axis, wherein each row comprises at least two of the electrodes;
   a longitudinal opening extending through the cuff body and further extending along an entire length of the cuff body, the longitudinal opening operable to receive a target nerve from a region outside of the stimulation cuff to within the nerve channel;
   a plurality of slots each extending through the cuff body and each having a slot length that extends more than 50%, but less than 100%, of the cuff length, wherein each of the slots is disposed between two of the rows of the electrodes with at least two of the electrodes of each of the two rows disposed adjacent opposing sides of the respective slot, wherein each of the slots is configured to permit tissue ingrowth, wherein the cuff body defines a perimeter around an entirety of each of the slots at both the interior surface and the exterior surface of the cuff body;

a lead body having a lead body axis; and a plurality of conductors extending through the lead body, mount and cuff, with the plurality of conductors electrically coupled to the electrodes.

13. The electrical stimulation lead of claim 12, wherein the slot length of each of the slots is more than 70% of the cuff length.

14. The electrical stimulation lead of claim 12, wherein each of the slots has a rectangular shape.

15. The electrical stimulation lead of claim 12, further comprising a mount disposed on the exterior surface of the cuff body and coupled to the lead body, wherein the lead body axis is radially offset from the nerve channel axis of the cuff body.

16. The electrical stimulation lead of claim 12, wherein the cuff body includes end portions configured to receive sutures.

17. The electrical stimulation lead of claim 12, further comprising cuff stiffeners embedded in the cuff body proximate the longitudinal opening, wherein the cuff stiffeners are made of rigid plastic.

18. The electrical stimulation lead of claim 17, wherein the cuff stiffeners are cylindrical.

19. An electrical stimulating system comprising:

the electrical stimulation lead of claim 12;

a control module coupleable to the electrical stimulation lead, the control module comprising a housing, and an electronic subassembly disposed in the housing; and a connector for receiving the electrical stimulation lead, the connector having a proximal end, a distal end, and a longitudinal length, the connector comprising a connector housing defining a port at the distal end of the connector, the port configured and arranged for receiving a proximal end of the lead body of the electrical stimulation lead, and a plurality of connector contacts disposed in the connector housing, the plurality of connector contacts configured and arranged to couple to at least one of a plurality of terminals disposed on a proximal end of the lead body of the electrical stimulation lead.

20. The electrical stimulation system of claim 19, further comprising a lead extension coupleable to both the electrical stimulation lead and the control module.

* * * * *